United States Patent [19]

Panigrahi et al.

[11] Patent Number: 5,981,590
[45] Date of Patent: Nov. 9, 1999

[54] ORAL GLUTAMINE IN THE PREVENTION OF NEONATAL NECROTIZING ENTEROCOLITIS AND OTHER GASTROINTESTINAL MUCOSAL DAMAGE

[75] Inventors: Pinaki Panigrahi, Laurel; Karoly Horvath, Baltimore; Ira H. Gewolb, Pikesville, all of Md.

[73] Assignee: ProBiotix, Inc., Baltimore, Md.

[21] Appl. No.: 08/819,624

[22] Filed: Mar. 17, 1997

[51] Int. Cl.$^6$ .............................................. A61K 31/195
[52] U.S. Cl. ................................................... 514/563
[58] Field of Search ........................................... 514/563

[56] References Cited

U.S. PATENT DOCUMENTS 5,288,703  2/1994  Wilmore ........................... 514/2

OTHER PUBLICATIONS

Glutamine and the Integrity of Intestinal Epithelial Cells: increased Bacterial Transcytosis through Epithelial Monolayers in the Absence of Glutamine. Panigrahi et al. Abstract for conference, May 14–17, 1995.
Alexander et al. Beneficial Effect . . . Ann.Surg. (abstract) 1980, 192, 505–517.
Alexander et al., Ann. Surg. (abstract) 1990, 212, 496–512.
Alverdy et al. Total parenteral nutrition promotes bacterial trans–location from the gut. Surgery. 1988, 104, 185–190 (abstract).
Ardawi et al. Glutamine metabolism in lymphocytes of the rat. Biochem. J. 1983, 212, 835–842.
Burke et al. Glutamine–supplemented total parenteral nutrition improves immune fraction. Arch. Surg. 1989, 124, 1396–1399 (abstract).
Deitch et al. Endotoxin promotes the translocation of bacteria from the gut. Arch. Surg. 1987, 122, 185 (abstract).
Deitch et al. Hemorrhagic shock induced bacterial translocation is re–duced by xanthine oxidase inhibition or inactivation. Surgery (abstract) 1988, 104.
Fox et al. Effect of a glutamine–supplemented enteral diet on metho–trexate–induced enterocolitis. J. Parent. Ent. Nutr. (abstract) 1988, 12, 325–331.
Ghishan et al. Glutamine transport by rat basolateral membrane vesicles. Biochim. Biophys. Acta. (abstract) 1989, 979, 77–81.
Guzman–Stein et al. Abdominal radiation causes bacterial translocation J. Surg. Res. (abstract) 1989, 46, 104.
Harzer et al. Human milk nonprotein nitrogen components . . . Am.J.Clin.Nutr. (abstract) 1984, 40, 303–309.
Horvath et al. Short–term effect of epidermal growth factor on sodium–cotransport . . . Biochim. Biophys. Acta. (abstract) 1994, 1222, 215–222.
Horvath et al. Glutamine–free oral diet and the morphology and function of the rat small intestine. J. Parent. Ent. Nutr. (abstract) 1996, 20, 128–130.
Hughes et al. Speed of onset of adaptive mucosal hypoplasia . . . Clin. Sci. 1980, 59, 317–327 (abstract).
Jones et al. Bacterial translocation and intestinal atrophy after injury and burn wound sepsis. Ann. Surg. 1990, 211, 399 (abstract).

Kimura RE. Glutamine oxidation by developing rat small intestine. Pediatr. Res. (abstract) 1987, 21, 214–217.
Kudsk et al. Enteral versus parental feeding: Effects on septic morbidity . . . Ann. Surg. 1992, 215, 503–513 (abstract).
Kueppers et al. Effect of total parental nutrition plus morphine on bacterial translocation in rats. Ann. Surg. 1993, 217, 286–292 (abstract).
Li et al. Addition of L–glutamine to total parental nutrition and its effect of portal insulin . . . J. Surg. Res. (abstract) 1990, 48, 421–426.
Moore et al. TEN versus TPN following major torso trauma; reduced septic morbidity. J. Trauma 1989, 29, 916–923 (abstract).
O'Dwyer et al. Maintenance of small bowel mucosa with glutamine enriched parental nutrition. JPEN 1989, 13, 579–585 (abstract).
Panigrahi et al. Development of an in vitro model for study of non–01 Vibrio Cholerae virulence using Caco–2 cells. Infect.Immun. (abstract0 1990, 58,3415–2.
Panigrahi et al. Occurrence of necrotizing enterocolitis may be dependent on patterns of bacterial adherence . . . Pediatr. Res. (abstract) 1994, 36, 115–121.
Panigrahi et al. Coli transcytosis in a Caco–2 cell model: implication in neonatal necrotizing enterocolitis. Ped. Res. 1996 (abstract).
Redan et al. Orgran distribution of gut–derived bacteria caused by bowel manipulation or ischemia. Am. J. Surg. 1990, 159, 85–89 (abstract).
Said et al. Transport characteristics of glutamine in human intestinal brush–border membrane vesicles. Am. J. Physiol. (abstract) 1989, 256, G240–G245.
Sedman et al. The prevalence of gut translocation in humans. Gastrenterology (abstract) 1994, 107, 643–649.
Souba et al. Oral glutamine reduces bacterial translocation following abdominal radiation. J. Surg. Res. 1990, 48, 1–5 (abstract).
Zielke et al. Reciprocal regulation of glucose and glutamine utilization by cultured human diploid fibroblasts. J. Cell Physiol. (abstract) 1978, 95, 41–48.
Panigrahi et al., J. Parent. Ent. Nutrition 21(2), 1997.

*Primary Examiner*—Phyllis G. Spivack
*Attorney, Agent, or Firm*—James Creighton Wray; Meera P. Narasimhan

[57] ABSTRACT

A method of preventing necrotizing tissue injury in the gastrointestinal tract comprising orally administering glutamine is disclosed. Glutamine protects tissues along the gastrointestinal tract by blocking translocation of bacterial agents such as gram (–) bacteria, other infectious agents, toxins, chemicals and injurious substances. The intraluminal/apical presence of the glutamine optimizes mucosal defense and increases nutrient absorption. Enteral glutamine is useful in treating neonatal necrotizing enterocolitis for reducing inflammation caused by bacterial translocation and injury. Oral glutamine is also useful in treating gastrointestinal dysfunctions. When glutamine is orally administered, it coats gastrointestinal mucosa thereby treating infectious and/or inflammatory conditions of the gastrointestinal tract. It is useful in treating pathologic conditions with lowered transepithelial electrical resistance (TEER) by acting as a curative agent.

14 Claims, 6 Drawing Sheets

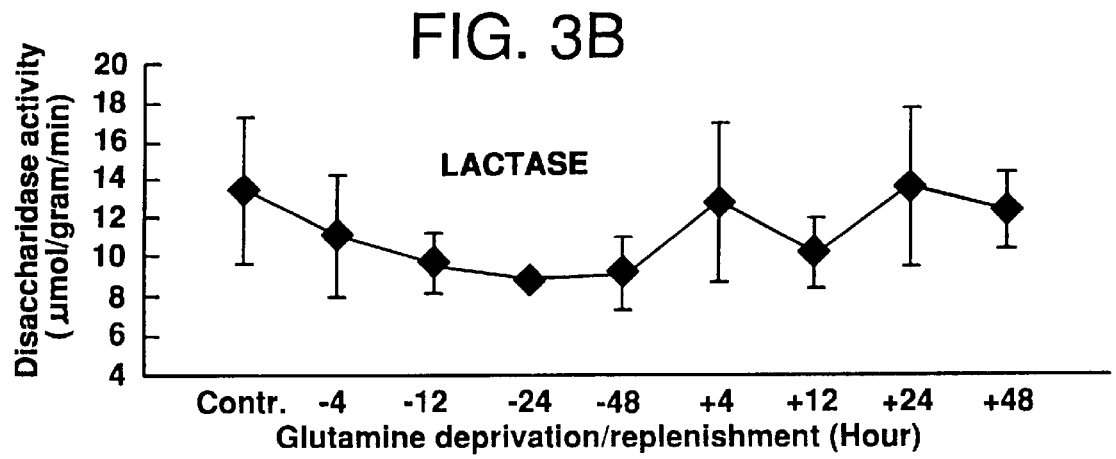
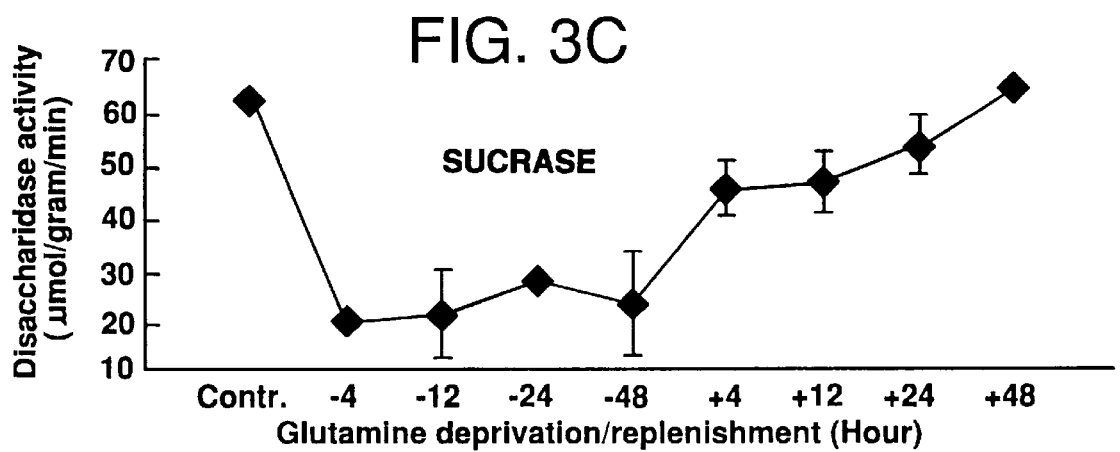
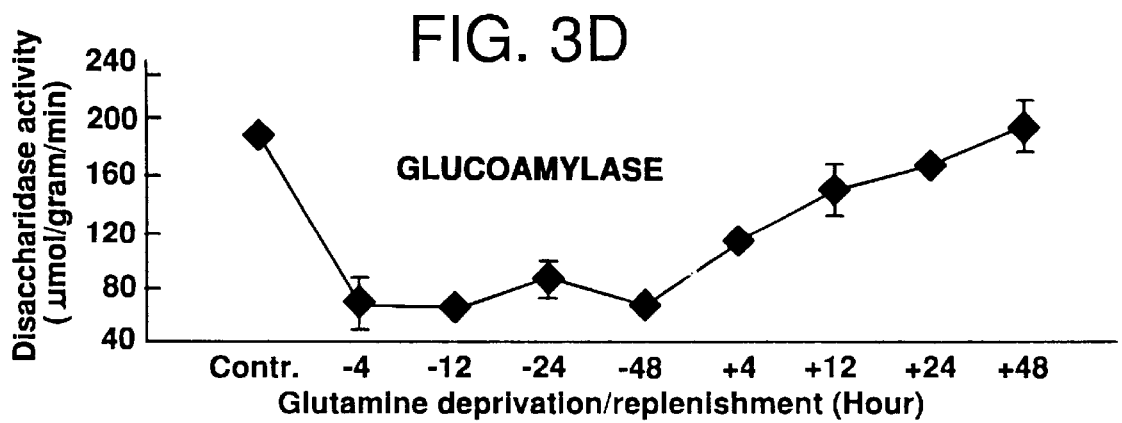

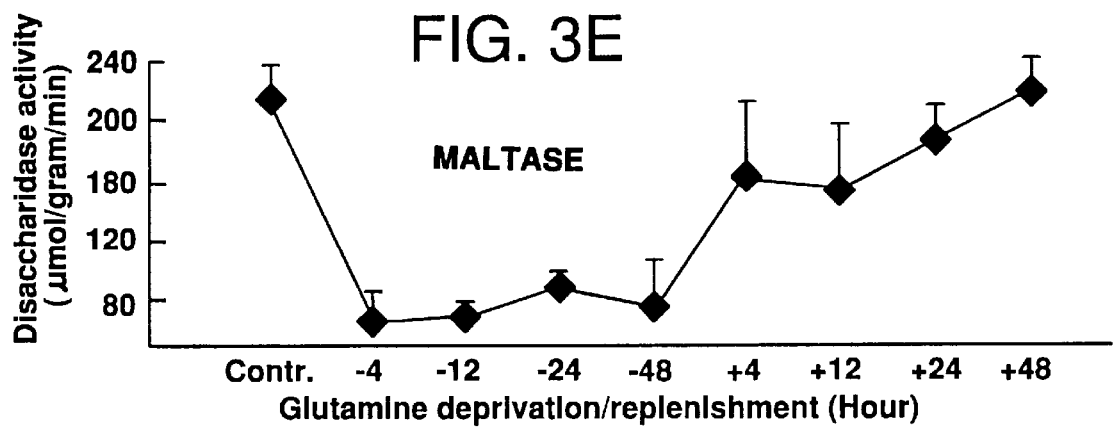
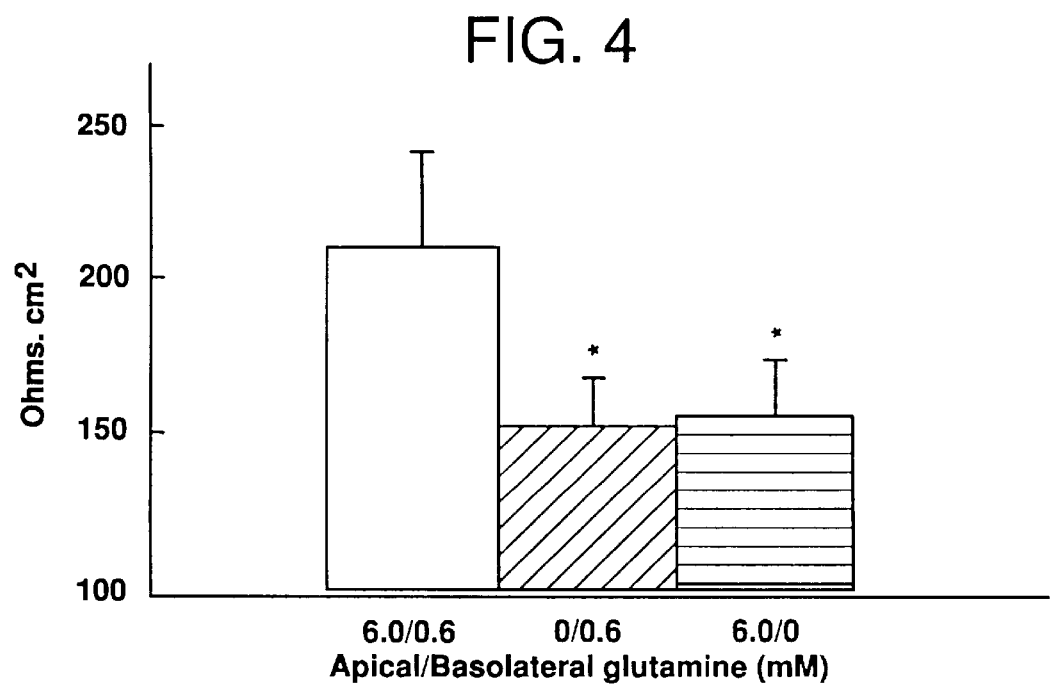

ORAL GLUTAMINE IN THE PREVENTION OF NEONATAL NECROTIZING ENTEROCOLITIS AND OTHER GASTROINTESTINAL MUCOSAL DAMAGE

FIELD OF THE INVENTION

The present invention is a method of using luminal glutamine in the prevention of bacterial translocation and Neonatal Necrotizing Enterocolitis (NEC) in vivo. The same treatment is useful to also protect intestinal cells against injuries caused by other infectious agents, toxins, chemicals, and injurious substances.

BACKGROUND OF THE INVENTION

Glutamine is a "conditionally essential amino acid": Although, glutamine is considered a non-essential amino acid, recent reports and studies from our laboratory support that the presence of intraluminal (apical) glutamine is essential for optimal intestinal epithelial function (Horváth K, Jami M M, Hill I D, Papadimitriou J C, Magder L S, Chanasongcram S. Glutamine-free oral diet and the morphology and function of the rat small intestine, *J Parent Ent Nutr* 1996;20: 128–134).

Small intestinal epithelial cells (enterocytes) have the third highest rate of cell turnover in the body, and require a constant high energy source. Glutamine is the preferred fuel for enterocytes (Williamson R C N. Intestinal adaptation. Structural, functional and cytokinetic changes, *N Engl J Med* 1978; 298:1393–1402; Nygaard K. Resection of the small intestine in rats. 3. Morphological changes in the intestinal tract. *Acta Chir Scand* 1967; 133: 233–248; Windmueller H G., Spaeth A E.: Uptake and metabolism of plasma glutamine by the small intestine. *J. Biol. Chem.* 1974; 249: 5070–5079).

The enterocytes are strongly dependent on an external glutamine supply, because of the small size of the mucosal glutamine pool in the small intestine (0.2 $\mu$mol/g of tissue) compared to liver (5.94 $\mu$mol/g) or skeletal muscle (3,3 $\mu$mol/g). The activity of mucosal glutamine synthetase is also extremely low (Windmueller H G., Spaeth A E.: Uptake and metabolism of plasma glutamine by the small intestine. *J. Biol. Chem.* 1974; 249: 5070–5079; Lund P.: A radiochemical assay for glutamine synthetase, and activity of the enzyme in the rat tissues. *Biochem. J.* 1970; 118:35–39).

Although enterocytes can get glutamine from both the lumen and circulating blood, these two sources of glutamine are not utilized in identical manner. During total parenteral nutrition (TPN) without glutamine, intestinal atrophy and hypofunction occurs within 3 days, despite the fact that L-glutamine levels in serum do not decrease significantly. Although L-glutamine is not regarded as an essential amino acid, its necessity during TPN makes it a conditionally essential amino acid in humans (Hughes C A, Dowling R H. Speed of onset of adaptive mucosal hypoplasia and hypofunction in the intestine of parenterally fed rats. *Clin Sci* 1980; 59:317–327).

Atrophy of the intestine also involves cells and organelles other than enterocyte. Immunological cells, such as lymphocytes and macrophages, in the mucosa also metabolize glutamine. Fibroblasts require glutamine for optimal function, as well (Ardawi M S M, Newsholme E A. Glutamine metabolism in lymphocytes of the rat. *Biochem J.* 1983; 212: 835–842; Caldwell M D. Local glutamine metabolism in wound and inflammation. *Metabolism* 1989; 38(suppl):34–39; Zielke H R, Ozand P T, Tildon J T, Sevdalian D A, Cornblath M. Reciprocal regulation of glucose and glutamine utilization by cultured human diploid fibroblasts. *J Cell Physiol* 1978; 95:41–48).

In the absence of glutamine the rate of ($^3$H) thymidine incorporation into DNA was very low in mesenteric lymphocytes and even a small amount of glutamine (1 $\mu$M) caused a four-fold increase in incorporation. TPN formulas without glutamine result in significant decrease in the secretory IgA level associated with bacterial translocation from the gut. 2% glutamine in TPN significantly decreased the bacterial (*E. coli, Proteus mirabilis*) translocation to mesenteric lymph nodes in rats (Burke D J, Alverdy J C, Aoys E, Moss G. Glutamine-supplemented total parenteral nutrition improves gut immune function. *Arch Surg* 1989; 124:1396–1399), although there was no significant difference in the adherence of bacteria to the ileum and colon (Ardawi M S M, Newsholme E A. Glutamine metabolism in lymphocytes of the rat. *Biochem J.* 1983; 212: 835–842; Alverdy J C, Chi H S, Sheldon G S. The effect of parenteral nutrition on gastrointestinal immunity, the importance of enteral stimulation. *Ann. Surg.* 1985; 202:681–684; Alverdy J C, Aoys E, Moss G S. Total parenteral nutrition promotes bacterial translocation from the gut. *Surgery* 1988; 104:185–190).

TPN supplemented with glutamine restored the normal SIgA levels in bile. Glutamine supplementation was also beneficial in models of mucosal damage (radiation, methotrexate) by significantly decreasing the mortality of animals and accelerating mucosal recovery. These data emphasize the importance of glutamine for two distinct functions of the small intestine: (I) nutrient absorption and (II) the mucosal defense (Burke D J, Alverdy J C, Aoys E, Moss G. Glutamine-supplemented total parenteral nutrition improves gut immune function. *Arch Surg* 1989; 124:1396–1399; Fox A D, Kripke S A, De Paula J, Berman J M, Settle R G, Rombeau J L. Effect of a glutamine-supplemented enteral diet on methotrexate-induced enterocolitis. *J Parent Enteral Nutr* 1988;12:325–331; Klimberg V S, Souba W W, Dolson D, Copeland E M. Oral glutamine supports crypt cell turnover and accelerates intestinal healing following abdominal radiation. *JPEN* 1989; 115:38 (abstract)).

Effects of Glutamine on the Small Intestinal Mucosa

Glutamine increases the number of mitoses per crypt in animals fed a glutamine-supplemented elemental diet. That implies that glutamine supports crypt cell turnover and leads to increased villous height. Burke et al demonstrated that the addition of glutamine to TPN resulted in the maintenance of normal levels of IgA (Barber A E, Jones W G, Minei J P, Moldawer L L, Fahey T J, Lowry S F, Shires G T. Composition and functional consequences of fiber and glutamine supplementation of enteral diets. *Surg Forum* 1989;40:15–16; Klimberg V S, Souba W W, Dolson D, Copeland E M. Oral glutamine supports crypt cell turnover and accelerates intestinal healing following abdominal radiation. *JPEN* 1989; 115:38 (abstract)). (Hwang T L, O'Dwyer S, Smith R J, Wilmore D W. Preservation of the small intestinal mucosa using glutamine supplemented parenteral nutrition. *Surg Forum* 1986; 37:56–58); Burke D J, Alverdy J C, Aoys E, Moss G. Glutamine-supplemented total parenteral nutrition improves gut immune function, 1989; 124:1396–1399).

Underlying mechanism of actions of glutamine on the intestinal mucosa are not known. Li et al reported an elevated concentration of glucagon in the portal vein of rats receiving glutamine containing TPN. Glucagon has an important role in the regulation of glutaminase. O'Dwyer suggested that the trophic effect of glutamine may be related to its secretagogue action, stimulating enteroglucagon secretion (Li S, Nussbaum M S, McFadden D W, Zhang F-S, LaFrance R J, Dayal R, Fischer J E. Addition of L-glutamine to total parenteral nutrition and its effect on portal insulin and glucagon and the development of hepatic steatosis in rats. *J Surg Res* 1990; 48:421–426); Geer R J, Williams P E, Lairmore T, Abumrad N N. Glucagon: an important stimulator of gut and hepatic glutamine metabolism. *Surg Forum* 1987; 38:27–28); O'Dwyer S T, Smith R J, Hwang T L, Wilmore D W. Maintenance of small bowel mucosa with glutamine enriched parenteral nutrition. *JPEN* 1989; 13:579–585).

Glutamine and the Neonatal Intestine

Very little data are available concerning the role of glutamine in the developing intestine. Kimura demonstrated an increased glutamine oxidation in the bowel of newborn rats compared to adult animals, indicating a higher demand for glutamine during development (Kimura R E. Glutamine oxidation by developing rat small intestine. *Pediatr Res* 1987; 21:214–217).

The glutamate content of human milk protein is very high and it is the most abundant amino acid in a variety of milk proteins (casein, serum albumin, lactoferrin, IgA and a-lactalbumin). Glutamine, glutamic acid and taurine are the most abundant free amino acids in human milk. Presumably, the high glutamate and glutamine content is advantageous for the developing small intestine (Harzer G, Bindels J G. Main compositional criteria of human milk and their implications on nutrition in early infancy. In: *New aspects of nutrition in pregnancy, infancy and prematurity*. (ed. Xanthou M). Elsevier Science Publishers, Amsterdam, 1987, p. 83–94; Rassin D K. Protein requirements in neonate. In: *Textbook of Gastroenterology and Nutrition in Infancy* (ed. Lebenthal E.), Raven Press, Ltd., New York, 1989, pp. 281–292; Harzer D, Franzke V, Bindels J G. Human milk nonprotein nitrogen components: changing patterns of free amino acid and urea in the course of early lactation. *Am J Clin Nutr* 1984; 40:303–309.

Very recently, Neu et al. have studied glutamine metabolism in preterm infants and have shown that preterm infants can tolerate and utilize glutamine when provided orally (enterally). Examining the immunological functions, these authors reported a reduced HLA-DR(+) T cell population and a concomitant increase in nosocomial infection in preterm infants not receiving supplemental oral glutamine.

Bacterial Translocation

Bacterial translocation is defined as the passage of viable intestinal bacteria across the intestinal epithelial cell layer into the normally sterile extra intestinal tissues. The translocated bacteria are usually normal inhabitants of the lower part of the small intestine and the colon. Translocation of bacteria may occur both transcellularly and paracellularly (Alexander J W, Bryce S T, Babock G F et al. The process of microbial translocation. *Ann Surg* 1990;212:496–512).

The first step in the process of translocation is the traffic of bacteria across the epithelial cell (enterocyte) monolayer. Translocation of few bacteria is a normal process and the mucosal immune system (macrophages as first line of defense) along with the consequent immune activation prevent further translocation. Secretory immunoglobulins may prevent the attachment of the same bacteria into the mucosal surface.

In the absence of glutamine (TPN) expression of secretory IgA is decreased. The Golgi-apparatus plays an important role in secretory IgA production. The production of secretory component takes place in the rough endoplasmic reticulum and it needs further maturation in the Golgi apparatus. The morphological changes in the Golgi-apparatus described by our group may explain the decreased SIgA production found in patients on TPN. Any decline in immune defense results in deeper invasion of bacteria, and they can be detected in the mesenteric lymph nodes, liver and spleen. (Horváth K, Jami M M, Hill I D, Papadimitriou J C, Magder L S, Chanasongcram S. Glutamine-free oral diet and the morphology and function of the rat small intestine. *J Parent Ent Nutr* 1996;20: 128–134; Burke D J, Alverdy J C, Aoys E, Moss G. Glutamine-supplemented total parenteral nutrition improves gut immune function. *Arch Surg* 1989; 124:1396–1399; Brandtzaeg P, Halstensen T S, Kett K, Kraj_i P, Kvale D, Rognum TO, Scott H, Sollid L M. Immunobiology and immunopathology of human gut mucosa: humoral immunity and intraepithelail lymphocytes. *Gastroenterology* 1989; 97:1562–84).

Necrotizing Enterocolitis in Premature Infants

NEC is the most serious gastrointestinal disorder of premature infants and one of the leading causes of death in neonatal intensive care units (NICU). It is the most common surgical emergency in the newborn period and the second leading cause of morbidity and mortality in the preterm population. The incidence of NEC in selected studies has ranged from fewer than 1% to as many as 5% of NICU admissions. A recent multicenter study of 2681 infants weighing 501–1500 grams reported that proven NEC (Bell Stage 2–3) occurred in 10.1% and suspected NEC (Bell Stage 1) in a further 17.2% of the cohort; mortality was 54% in infants with severe (Stage 3) NEC.

Those data indicate that NEC is a major public health problem in neonates: given the ~4 million births/year in the United States, NEC would be expected to develop in 1200–9600 infants, of whom between 9–28% will die as a result of their disease. Earlier studies indicated a mortality of 10–55% in premature infants. Survivors of NEC can also have considerable long-term morbidity resulting from their disease, including short-gut syndrome, failure-to-thrive, intestinal stricture, and the need for repeated surgery.

Clinical Significance

Several studies have demonstrated the beneficial effect of glutamine in the intestine and especially on enterocytes (Barber A E, Jones W G, Minei J P, Moldawer L L, Fahey T J, Lowry S F, Shires G T. Composition and functional consequences of fiber and glutamine supplementation of enteral diets. *Surg Forum* 1989;40:15–16; Klimberg V S, Souba W W, Dolson D, Copeland E M). Oral glutamine supports crypt cell turnover and accelerates intestinal healing following abdominal radiation. *JPEN* 1989; 115:38 (abstract); Souba W W, Klimberg V S, Hautamaki R D, Meddenhall W H, Bova F C, Howard R J, Bland K I, Copeland E M. Oral glutamine reduces bacterial translocation following abdominal radiation. *J Surg Res* 1990; 48:1–5), however, the molecular mechanism of these effects has not been clarified. (Hwang T L, O'Dwyer S, Smith R J, Wilmore D W. Preservation of the small intestinal mucosa using glutamine supplemented parenteral nutrition. *Surg Forum* 1986; 37:56–58).

In different experimental animal models it has been shown that endotoxemia, ischemia, hemorrhagic shock can cause bacterial translocation. (Deitch E A, Berg R D, Specian R. Endotoxin promotes the translocation of bacteria from the gut. *Arch Surg* 1987; 122:185; Redan J A, Rush B F, Lysz T W, Smith S, Machiedo G W. Organ distribution of gut-derived bacteria caused by bowel manipulation or ischemia. *Am J Surg* 1990;159:85–89; Deitch E A, Bridges W, Baker J, Ma J W, Ma I, Grisham M B, Grenger D N, Specian R D, Berg R D). Hemorrhagic shock induced bacterial translocation is reduced by xanthine oxidase inhibition or inactivation. *Surgery* 1988; 104:191), burn and infection, chemotherapy, abdominal radiation. (Jones II W G, Minei J P, Barber A E, Raybern J, Fahey III T J, Shires III G T, Shires G T. Bacterial translocation and intestinal atrophy after injury and burn wound sepsis. *Ann Surg* 1990;211:399; Berg R D. Bacterial translocation from the gastrointestinal tract of mice receiving immunosuppressive chemotherapeutic agents. *Curr Microbiol* 1983; 8: 285–289; Fox A D, Kripke S A, De Paula J, Berman J M, Settle R G, Rombeau J L. Effect of a glutamine-supplemented enteral diet on methotrexate-induced enterocolitis. *J Parent Enteral Nutr* 1988;12:325–331; Guzman-Stein G, Bonsack M, Liberty J, Delaney J P). Abdominal radiation causes bacterial translocation, total parenteral nutrition, total parenteral nutrition plus narcotics and impaired intestinal motility can cause bacterial translocation to mesenteric lymph nodes, abdominal cavity, liver, spleen and blood resulting in septicemia and death. The cause of such increased bacterial translocation has not been defined. (*J Surg Res* 1989;46:104; Souba W W, Klimberg V S, Hautamaki R D, Meddenhall W H, Bova F C, Howard R J, Bland K I, Copeland E M. Oral glutamine reduces bacterial translocation following abdominal radiation. *J Surg Res* 1990; 48:1–5; Alverdy J C, Aoys E, Moss G S. Total parenteral nutrition promotes bacterial translocation from the gut. *Surgery* 1988; 104:185–190; Kueppers P M, Miller T A, Chen C Y K et al . . . Effect of total parenteral nutrition plus morphine on bacterial translocation in rats. *Ann Surg* 1993;217:286–292).

Prospective randomized clinical trials have documented that the incidence of major infectious complications is less in enterally fed burn and trauma, patients than in comparable patients fed parenterally. (Alexander J W, MacMillan J C, Stinnet J D. et al. Beneficial effect of aggressive protein feeding in severely burned children. *Ann Surg* 1980; 192:505–517; Kudsk K A, Groce M A, Fabian T C et al. Enteral versus parenteral feeding: Effects on septic morbidity after blunt and penetrating abdominal trauma. *Ann Surg* 1992; 215:503–513; Moore F A., Moore E E, Jones T N et al. TEN versus TPN following major torso trauma: reduced septic morbidity. *J Trauma* 1989; 29:916–923).

Sedman et al examined 242 general surgical patients for bacterial translocation during surgery. 10.3% of the patients had translocation detected on the intestinal serosa or in the mesenteric lymph nodes. Intestinal obstruction and inflammatory bowel disease were predisposing factors for translocation, however, 5% of patients without these conditions had translocation. The development of postoperative septic complications was twice as common in patients with translocation as those without it. (Sedman P C, Macfie J, Sagar P, Mitchell C J, May J, Mancey-Jones B, Johnstone D. The prevalence of gut translocation in humans. *Gastroenterology* 1994;107:643–649).

SUMMARY OF THE INVENTION

Based on our Caco 2 cell and ileal loop models, the instant invention demonstrates that the absence of luminal glutamine results in NEC and mucosal damage.

An object of the present invention is to treat premature infants with additional glutamine from the enteral side (oral administration) to reduce bacterial translocation and subsequent development of NEC.

A second object is to use similar strategy (high oral glutamine) in adult and pediatric patients in intensive care units under total parenteral nutrition (intravenous feed) to avoid mucosal dysfunction and further bacterial translocation.

A third object is its use in patients undergoing chemotherapy, irradiation and bone marrow transplantation.

Yet another object is to use the preparation to prevent or treat other inflammatory mucosal diseases of the GI tract that may have a bacterial etiologic component.

Another object is the use in post surgical patients during diet restriction and parenteral nutrition. In these patients the translocation of intestinal bacteria may result in systemic sepsis and multi organ failure without glutamine therapy.

A further object is to use the preparation in fullterms, children, and adults, in GI dysfunctions of infective and/or inflammatory origin where bacterial translocation may act as a trigger or aid in disease progression.

A preferred method of preventing necrotizing tissue injury in gastro-intestinal tract comprises orally administering glutamine. The tissues are protected along the gastro-intestinal tract by blocking bacterial translocation with the glutamine.

Preferably, the tissues along the gastro-intestinal tract are protected with the administered glutamine which blocks translocating of bacteria (such as gram (–) bacteria), other infectious agents, toxins, chemicals, and injurious substances. Oral glutamine also optimizes mucosal defense and increases nutrient absorption due to its intraluminal/apical availability. Glutamine is administered for preventing and treating gastro-intestinal dysfunctions and pathologic conditions.

Glutamine may be administered to individuals such as pre-term infants, full-term infants, children and adults. Glutamine may be provided in any form that is orally administrable. That includes powder forms or in a reconstituted mixture with a fluid. Alternately glutamine may be administered as capsules. Preferably, the capsules are acid resistant slow-release release micro-capsules which last long enough to reach the requisite areas in the gastro-intestinal tract such as the intestines. The capsules may be enter coated time-release capsules. Also, other drugs for treatment of ailments may be administered with the glutamine.

A preferred method of treating neonatal necrotizing enterocolitis comprises providing enteral glutamine for reducing inflammation caused by bacterial adherence, invasion and injury.

A preferred method of treating gastro-intestinal dysfunctions includes providing apical glutamine for improving physiological functions.

Preferably, the oral administration allows the glutamine to coat gastro-intestinal mucosa thereby treating infectious and/or inflammatory conditions of the gastro-intestinal tract.

A preferred method of treating pathologic conditions with lowered transepithelial electrical resistance (TEER) is by administering oral glutamine as a curative agent.

These and further and other objects and features of the invention are apparent in the disclosure, which includes the above and ongoing written specification, with the claims and the drawings.

BRIEF DESCRIPTION OF THE ILLUSTRATIONS

FIGS. 3A–E illustrate the Disaccharidase and glucoamylase activity during glutamine deprivation and replenishment.

FIG. 4 shows the results of both apical (0/0.6) and basolateral (6.0/0) glutamine deprivation.

Figure 5:
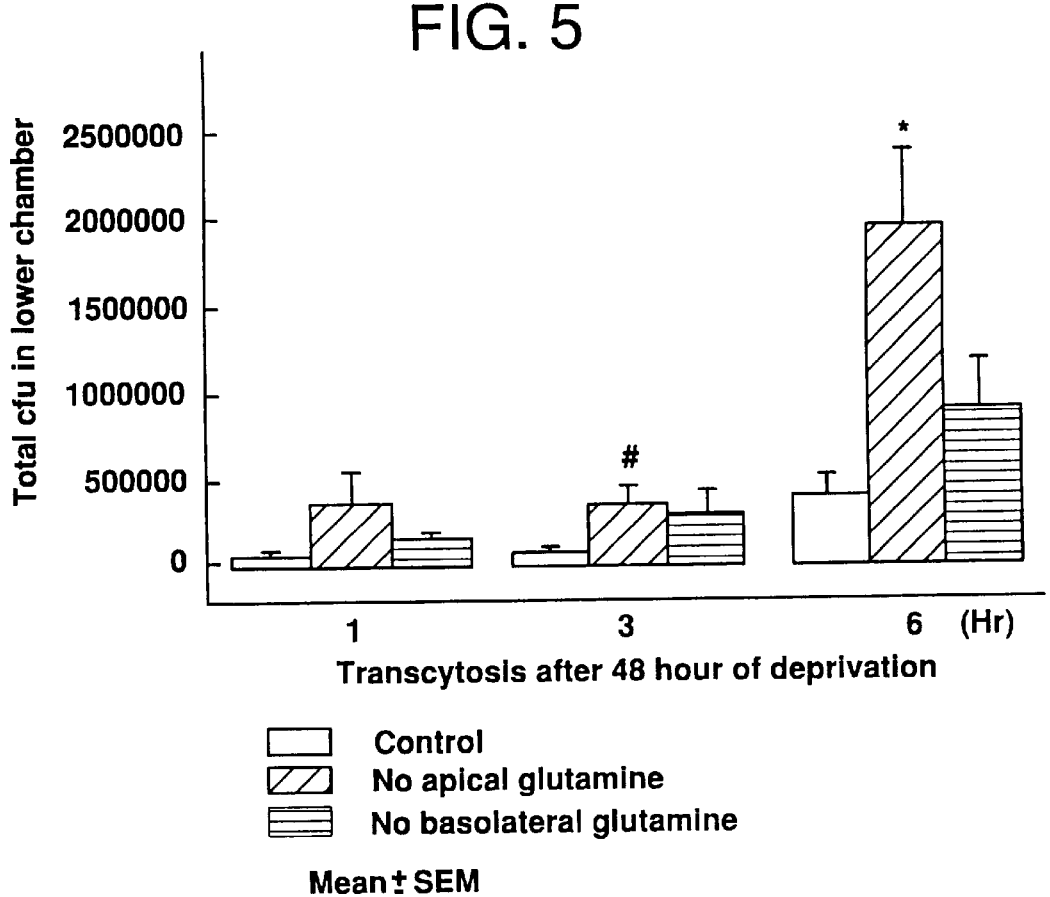

FIG. 5 shows the effect of apical vs. basolateral glutamine deprivation on bacterial transcytosis.

Figure 6:
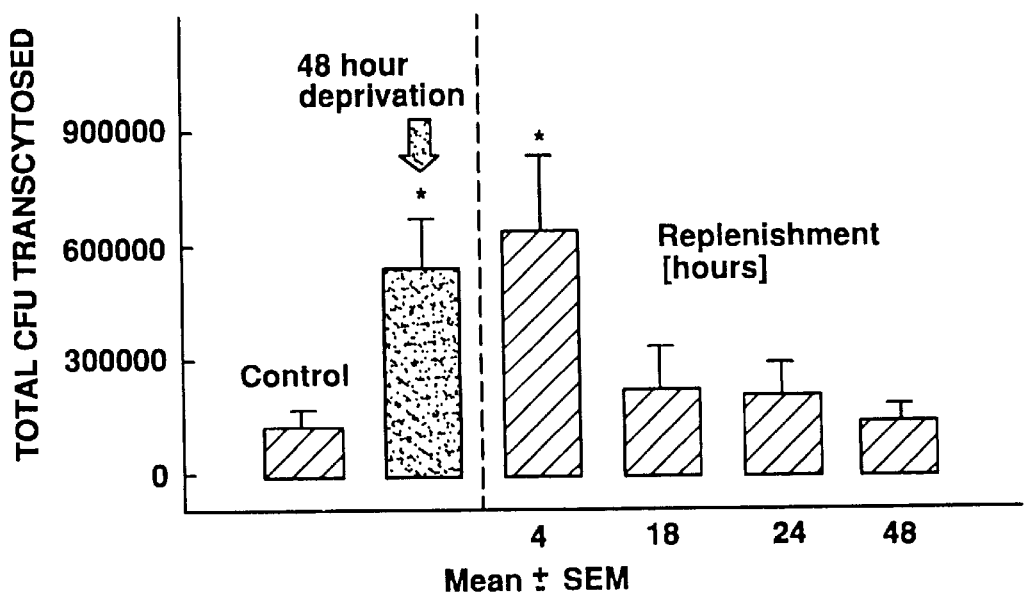

FIG. 6 shows the effect of glutamine replenishment.

Figure 7A:
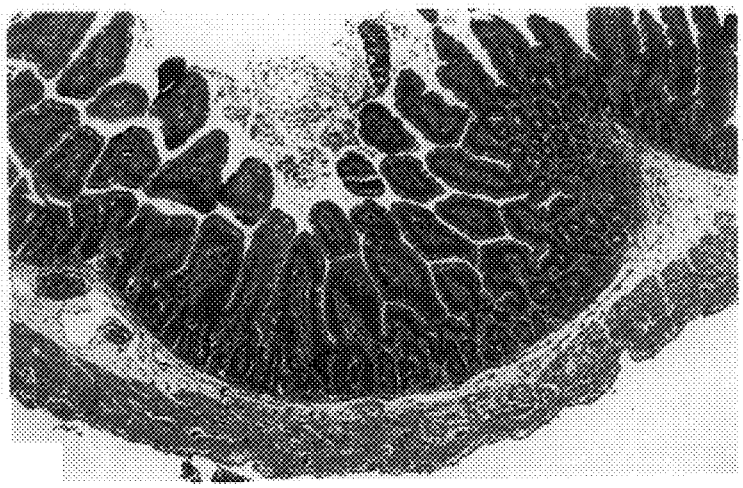
Figure 7B:
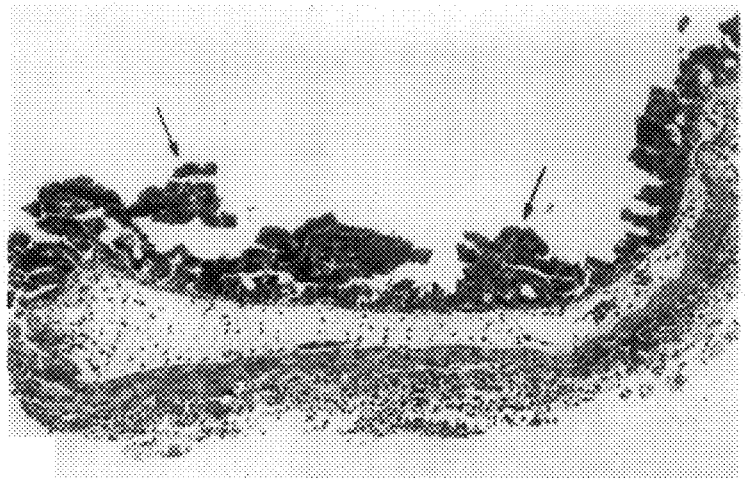
Figure 7C:
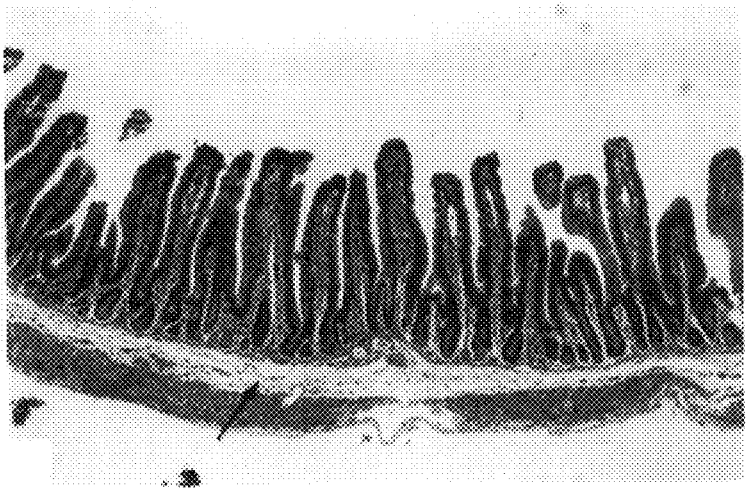

FIGS. 7A, 7B, and 7C show the histopathology of weanling rabbit ileal loops:

7A: shows control loops inoculated with PBS;

7B: shows loops inoculated with $10^9$ CFU of *E. coli* strain 21-1 isolated from a patient with NEC.

7C: shows loops co-inoculated with 4 mM glutamine and $10^9$ CFU of *E. coli*.

DETAILED DESCRIPTION OF THE PREFERRED EMBODIMENTS

In the present invention, supply of glutamine from the luminal side (apically for the enterocytes) has been shown to reduce bacterial translocation and maintain healthy physiological functions.

The present inventors show that supply of glutamine to the enterocytes from the apical side (luminal) is much more important and is critical in the maintenance of physiological functions. Lack of such apical glutamine results in decreased transepithelial resistance, increased passage of inulin, and increased bacterial translocation across intestinal cell monolayers. The present invention also demonstrates that it is not an energy related phenomenon, since, the deleterious effects are most remarkable 24–48 hr after glutamine deprivation. The present invention shows that these effects can be reversed in the same system by replenishment with glutamine, a process that again takes more than 24 hr for full recovery. These data underline that the present inventors have identified a novel phenomenon of glutamine action on enterocytes.

The underlying mechanisms as to why enterocytes cannot utilize glutamine from the basolateral side remains unsolved. However, these tissue culture results have been replicated in a weanling rabbit ileal loop model of NEC.

Effect of Glutamine on enterocytes in general is not critical to the present invention. It is well known that this amino acid is the major energy source for enterocytes. In humans, and experimental animal models the beneficial role of glutamine has been shown to be mediated via improved immunological functions. In the present invention, however, it is demonstrated for the first time, that due to some unknown cellular mechanisms enterocytes use glutamine much more efficiently when supplied from apical (luminal) side.

From a clinical stand point the present invention also demonstrates that lack of apical glutamine results in increased bacterial translocation in tissue culture systems. Translating the effects in vivo, instillation of rabbit loops with glutamine protects them against bactrial infections, such as the Gram (−) bacteria-induced necrotizing enterocolitis.

Figure 1:
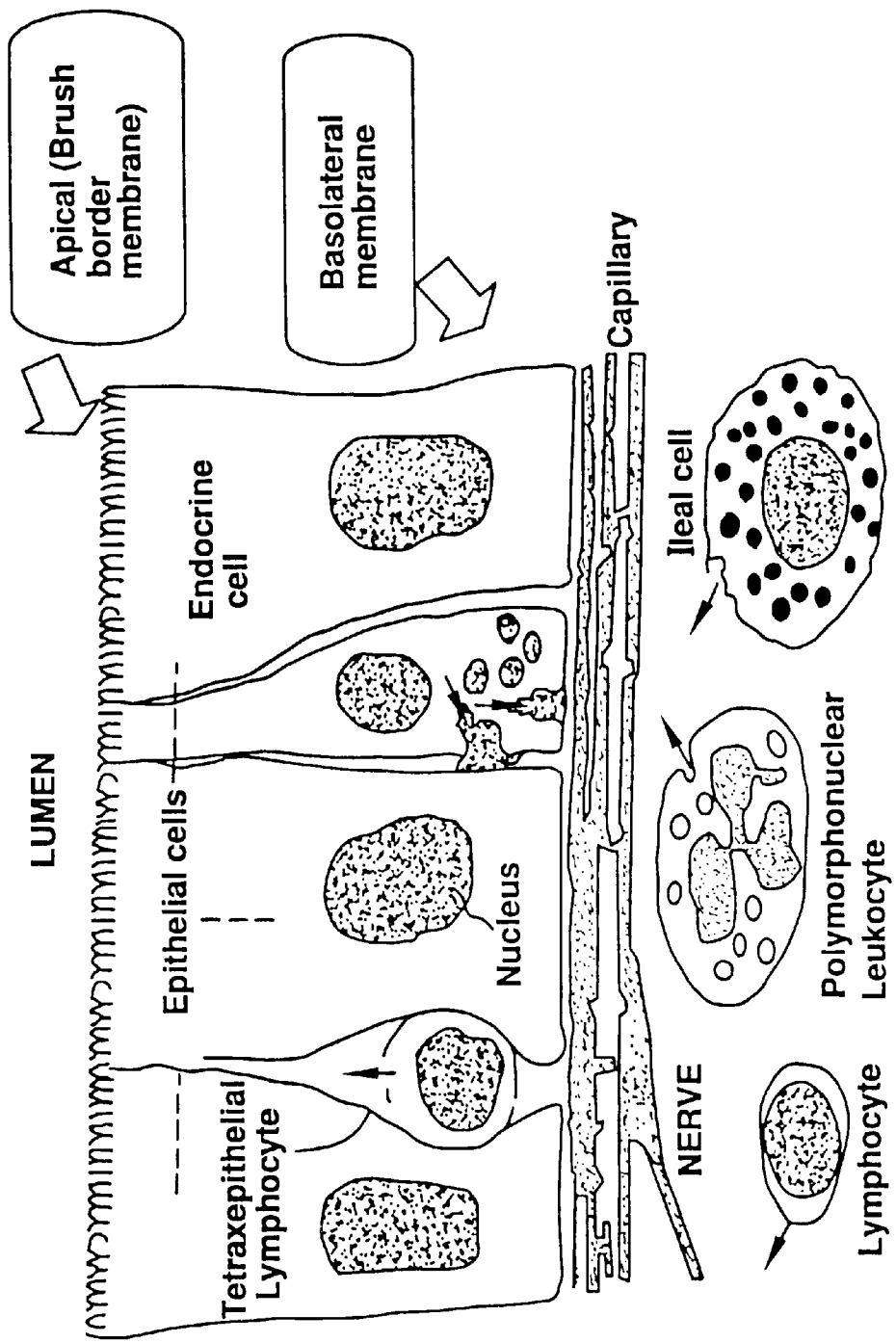
FIG. 1 is a schematic representation of an enterocyte with apical and basolateral sides.

The accompanying figures illustrate the following:

FIG. 1: Schematic representation of an enterocyte with apical and basolateral sides.

Figure 2:
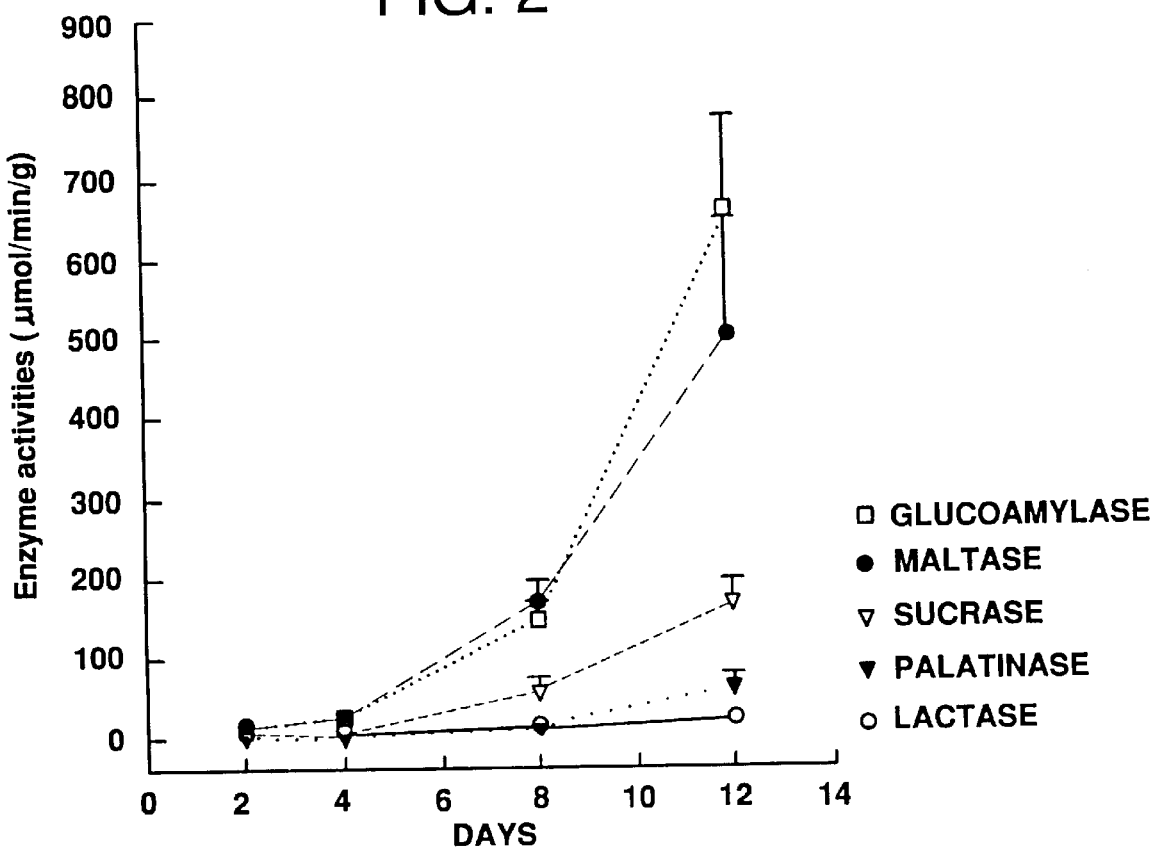
FIG. 2 shows the expression of disaccharidases as the Caco-2 cells differentiate.

FIG. 2: shows the expression of disaccharidases as the Caco-2 cells differentiate. Note the increase in enzyme expression after day-8 that reaches high levels comparable to human biopsy samples by day-12.

FIGS. 3A–E: FIGS. 3B–E: Disaccharidase and glucoamylase activity during glutamine deprivation and replenishment. There was a decline in the levels of all enzymes after 4 hr deprivation. While the drop in lactase did not reach statistical significance, all other values at time points from 4–48 hr deprivation were significantly different from control, $p<0.05$ (n=4). There was a linear increase in enzyme expression over the 4–48 hr replenishment period that reached base line level after 48 hr. The 4–48 hr values were not statistically different from the control, $p<0.05$ (n=4).

Figure 3A:
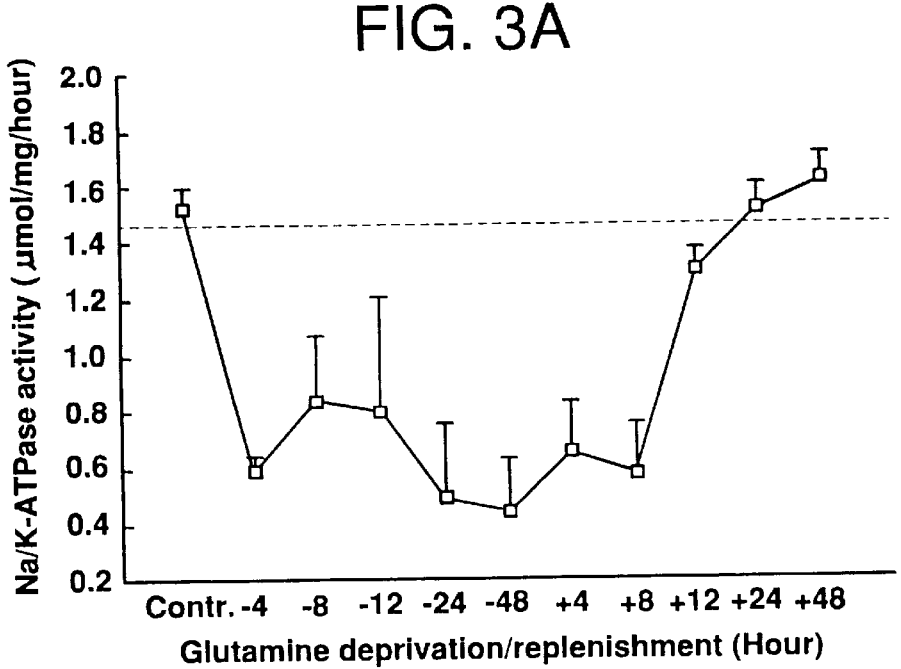

FIG. 3A: A drop in $Na^+/K^+$-ATPase activity was also noted as early as 4 hr glutamine deprivation, and continued to be significantly lower for 48 hr, $p<0.01$ (n=4). Replenishment-induced rise was significant only after 12 hr $(p,0.01)$ reaching baselines after 24 hr.

FIG. 4: Both apical (0/0.6) and basolateral (6.0/0) glutamine deprivation resulted in a significantly reduced TEER compared to control monolayers. $*=p<0.01$, apical deprivation and basolateral deprivation vs. control. There was no statistically significant difference between the apical and basolateral deprivations (n=4–7).

FIG. 5: Effect of apical vs. basolateral glutamine deprivation on bacterial transcytosis. There was a linear rise in bacterial translocation after at 1, 3, and 6 hr after infection following 48 hr of apical glutamine deprivation. At hr 3 and 6 there was a statistically significant rise in transcytosis with apical deprivation; $\#=p<0.05$, 3 hr apical deprivation vs. 3 hr control; $*=p<0.01$, 6 hr apical deprivation vs. 6 hr control (n=4–7).

FIG. 6: Effect of glutamine replenishment. There was a significant rise in transcytosis after 48 hr of deprivation that continued for 4 hr post-replenishment. Glutamine replenishment for 18 hr causes a significant drop in bacterial translocation, that reaches base line level after 48 hr. $*=p<0.01$, 48 hr deprivation and 4 hr replenishment vs. control (n=9–18).

FIG. 7: Histopathology of weanling rabbit ileal loops. A: control loops inoculated with PBS showing healthy villi and deeper layers (original magnification 40×). B: Loop inoculated with $10^9$ CFU of *E. coli* strain 21-1 isolated from a patient with NEC. There is severe damage to mucosa with massive submucosal edema and infiltration of polymorphonuclear cells into the lamina propria. C: Loop co-inoculated with 4 mM glutamine and $10^9$ CFU of *E. coli*. Note the near-total protection except a generalized mild submucosal edema.

EXAMPLE 1

Caco-2 Cell Culture Model

Effect of glutamine-deprivation was studied in Caco-2 cells derived from human adenocarcinoma cells which show all the morphological and functional characteristics of mature small intestinal epithelial cells after differentiation. In our system, similar results with high enzyme activity was observed after 10–12 days of growth (FIG. 2). When the fully differentiated Caco-2 cells were kept in a glutamine-free medium for 48 hours, it was found that a significant decrease in the brush border membrane enzyme (disaccharidases and glucoamylase) (FIGS. 3B–E), and in the ($Na^+$, $K^+$-ATPase) (FIG. 3A) enzyme activities (FIG. 3) occurred. The inventors observed a drop in transepithelial electrical resistance across the cell monolayer when the cells were deprived of glutamine either from the apical or basolateral side (FIG. 4). (Panigrahi P, Tall B D, Russell R G, DeTolla L J, Morris Jr J G Development of an in vitro model for study of non-O1 Vibrio cholerae virulence using Caco-2 cells. *Infect Immun* 1990; 58:3415–3424; Panigrahi P, Gupta S, Gewolb I H, Morris J G. Occurrence of necrotizing enterocolitis may be depenedent on patterns of bacterial adherence and intestinal colonization: studies in Caco-2 tissue culture and weanling rabbit models. *Pediatr Res* 1994;36:115–121; Panigrahi P, Bamford P, Horvath K, Glenn Morris J, Gewolb I H. *E. Coli* transcytosis in a Caco-2 cell model: implications in neonatal necrotizing enterocolitis. *Ped res* 1996; 40:415–421; Pinto M S, Robine-Leon M D, Appay M et al. Enterocyte-like differentiation and polarization of the human colon carcinoma cell line Caco-2 in culture. *Biol Cell* 1983;47:323–330).

EXAMPLE 2

Bacterial Translocation In Caco-2 Transwell System

Bacterial translocation was measured in the same condition using cells grown on polycarbonate filters. When cells were deprived of glutamine from the apical side, there was a ~10 and 5-fold increase in bacterial transcytosis in the $1^{st}$ and $6^{th}$ hr respectively (FIG. 5). Replenishment of apical glutamine resulted in the restoration of the bacterial translocation to the normal level after 18 hours (FIG. 6). *E. Coli* strain 21-1 isolated from an infant with necrotizing enterocolitis was used for this study. This in vitro system eliminates the confounding effects of immune system, and these results for the first time, demonstrate that glutamine primarily affects the enterocytes and thus influences initial steps of bacterial translocation. Note the effect of replenishment evident only after 18 hrs. The transcytosis level comes to baseline after 48 hrs. To further complement these results, intracellular ATP concentration was assayed using the commercial Sigma kit. There was no significant change in the ATP levels of Caco-2 cells treated with or without glutamine, except a transient increase after 4 hr in the glutamine deprived cells. These results indicate that there is a preferential effect of glutamine when it is supplied to the enterocytes from the apical (luminal) side, and that it is a more complex action on the cells than a simple energy-related phenomenon.

EXAMPLE 3

In vivo Weanling Rabbit Ileal Loop Studies

Following standard protocols ileal loop studies were conducted in weanling rabbits. Weanling rabbits between 350–400 gm were used. Surgical and inoculation procedures, essentially identical to our previously described methods were followed. 1 and 4 mM glutamine was used in the treated loops along with the *E. coli* strain. Non-infected loops inoculated with PBS and *E. coli* alone, were maintained in each animal as negative and positive controls. There was total protection against *E. coli* induced damaged in the loops receiving both concentrations of glutamine (FIG. 7). (Panigrahi P, Gupta S, Gewolb I H, Morris J G. Occurrence of necrotizing enterocolitis may be depenedent on patterns of bacterial adherence and intestinal colonization: studies in Caco-2 tissue culture and weanling rabbit models. Pediatr Res 1994;36:115–121).

An *E. coli* strain isolated from an infant with necrotizing enterocolitis (NEC) (laboratory strain 21-1) was used for in vitro translocation studies in Caco-2 cells and in the weanling rabbit ileal loop experiments.

Caco-2 Cell Culture System

Caco-2 cells were grown in Dulbecco's modified Eagle's medium (DMEM) supplemented with 1% nonessential amino acids, 1% sodium pyruvate, 10% fetal calf serum (FCS), 100 U of penicillin and 100 µg of streptomycin/mL in a 5% $CO_2$ atmosphere at 37° C. Glutamine supplementation was done according to the defined experimental conditions. For enzyme analysis, $3\times10^1$ cells were seeded onto 60-mm tissue culture dishes and grown for 12 days. For transcytosis studies, $0.2\times10^6$ cells in 0.3 mL medium were seeded on the apical side of 0.6-$cm^2$ polycarbonate transwell filters/clusters (Costar, Cambridge, Mass.). Each basolateral chamber received 1 mL of medium. Medium was changed every third day.

Caco-2 Cell Growth and Replication

At different days postconfluence, cells were counted in a hemocytometer after trypsinizing the monolayers. Total DNA content was measured by the perchloric acid method.

Monolayer Permeability and Integrity

Transepithelial electrical resistance (TEER) and inulin transport were examined to evaluate the structural integrity of the Caco-2 cell monolayer during days 2 to 14 postseeding. A Milli Cell ERS (Millipore) apparatus was used according to manufacturer's instructions to record the electrical resistance across cell monolayers. A polycarbonate membrane alone with media on both the apical and basolateral sides was used as control, and resistance was calculated in ohms per square centimeter.

Enzyme Estimation in Caco-2 Cells

Expression of brush border marker enzymes has been reported from various laboratories including ours. For this study, differentiated Caco-2 cells were washed in chilled phosphate buffered saline (PBS), harvested using a rubber policeman, centrifuged at 3000×g for 5 minutes; the cell pellets were stored frozen. Disaccharidase (sucrase, maltase, lactase, and palatinase) activities were determined by the method of Dahlquist. Glucoamylase was assayed by the method of Azad et al using maltooligosaccharide mixture (3 to 10 glucose units) as substrate (ICN, Irvine, Calif.). Protein content of the cell pellets was measured by Bradford Coomassie assay (Pierce Co, Rocldord, Ill.) and was used as an internal control. A time course glutamine deprivation/replenishment experiment was conducted.

Examination of "Apical vs Basolateral" Effect of Glutamine

Three defined experimental conditions were created and used in the transwell system for transcytosis studies; (1) control (6.0:0.6): 6 mmol/L glutamine in the upper chamber, 0.6 mmol/L in the lower chamber (considering that the basolateral side receives glutamine at a physiologic concentration of 0.6 mmol/L, and the upper chamber receives high glutamine found in the lumen); (2) apical deprivation (0:0.6): 0 mmol/L glutamine in the upper chamber, 0.6 mmol/L in the lower chamber; and (3) basolateral deprivation (6.0:0): 6 mmol/L glutamine in the upper chamber, 0 mmol/L in the lower chamber. After glutamine deprivation and replenishment over different time points, translocation studies were carried out over a I- to 6-hour period. Clusters were transferred to a fresh well containing DMEM at the end of each incubation period.

Bacterial Transcytosis Study

Transwell clusters were washed in sterile PBS and refed with fresh DMEM without antibiotics or FCS. TEER was measured, and $3\times10^1$ CFU of the bacterial strains were applied to the apical side in 0.3 mL of DMEM. After gentle agitation for 10 minutes, the clusters were incubated for 6 hours. At the end of each hour, clusters were transferred to a new well containing fresh DMEM; samples were obtained at the end of the different incubation periods from the basolateral side and quantitated by plating dilutions on L-agar plates. Colonies were counted after overnight incubation of the plates at 37° C. *S. typhimurium* strain SO 1344 and *E. coli* strain DH5-α were used as controls.

To examine the effect of glutamine replenishment, after 48 hours of glutamine deprivation, monolayers were refed with fresh DMEM containing 6 mmol/L glutamine. Translocation experiments were carried out after 4, 18, 24, and 48 hours of replenishment.

Ileal Loop Model in Weanling Rabbit

Ileal loops were prepared in weanling New Zealand white rabbits weighing <500 g following our previously described methods. *E. coli* strain 21-1 ($10^9$ CFU) with or without different concentrations of glutamine (1 and 4 mmol/L) was inoculated in duplicate animals, in duplicate loops. Control loops were maintained in each animal that received PBS only. Rabbits were killed after 16 to 18 hours, gross changes in the loops noted, fluid accumulation measured, and tissue samples fixed in formalin for histopathology. Only the center portion of the loop sufficiently away from the ligature sites was collected to avoid any local inflammatory changes caused by physical trauma. All studies were approved by the Institutional Animal Care and Use Committee of the University of Maryland at Baltimore.

Statistical Analysis

Statistical Analysis was performed using Student's t test and analysis of variance (ANOVA) with Student-Newman-Keuls or Dunnett's (for multiple comparisons to controls) post hoc test using SigmaStat (Jandel Scientific, San Rafael, Calif.). A p value of <0.05 was considered statistically significant.

Effect of Glutamine on Caco-2 Cell Growth and Replication

Glutamine had no effect on cell growth or multiplication. There was no significant difference between the cell count and the DNA content of the monolayers grown with or without glutamine during the 12-day period (data not shown). However, there was a significant decline in the total protein content of the glutamine-deprived cells.

Effect of Glutamine on Enterocyte Enzyme Expression

There was a decline in the expression of all enzymes tested after 4 hours of glutamine deprivation, which reached a nadir at 24 to 48 hours (FIG. 3 top panel). A linear increase in expression of disaccharidases was noted over 4 to 48 hours during replenishment (FIG. 3 top panel). However, the recovery of ATPase occurred only after 12 hours, reaching baselines after 24 to 48 hours (FIG. 3 bottom panel).

Monolayer Permeability and Integrity

Two-day-old postconfluent monolayers showed development of high TEER ($172\pm20.2$ $\Omega/cm^2$), comparable to the TEER of intact human gastrointestinal mucosa, which was maintained over the 12-day period. Glutamine deprivation resulted in decreased TEER of the monolayers. Both apical and basolateral deprivation resulted in significant decreases in the TEER compared with controls. There was no statistical difference in the TEER between apical and basolateral deprivation (FIG. 4).

Bacterial Translocation

Glutamine deprivation resulted in increased *E. coli* translocation, and the increase reached statistical significance after 48 hours of deprivation. Further experiments were conducted after 48-hour deprivation only and *E. coli* translocation were noted over a 1–6 hour period. No difference could be noted between control and glutamine-deprived cells after 1 hour. After 3 and 6 hours, there was a statistically significant increase in bacterial transcytosis with apical deprivation. Although there was a rise in transcytosis, statistical significance was not observed after basolateral deprivation at hours 3 and 6 (FIG. 5). Upon replenishment with glutamine, there was no corrective effect during the first 12-hour period (6- and 12-hour data not shown); however, the level of transcytosis reduced to normal levels after 18 hours. Although the baseline was reached after 48 hours, there was no statistically significant difference between control and 18-, 24- , and 48-hour replenishment (FIG. 6).

Effect of Glutamine in the Mucosal Injury Model in Weanling Rabbit

*E. coli* infection produced typical necrotic injury in the ileal loops (FIG. 7). There was severe damage, necrosis, and hemorrhage of mucosa, in cases resulting in total collapse. There was also massive submucosal edema, with infiltration of polymorphonuclear cells into submucosa and lamina propria. Loops receiving 1 and 4 mmol/L glutamine showed an almost total protection against *E. coli*-induced injury. No further higher concentration of glutamine was used. There were some acute inflammatory changes and mild submucosal edema with intact mucosa and deeper layers. Fluid accumulation was minimal (2 to 3 mL) and was noted in all of the loops including the control loops receiving PBS alone.

A preferred range of oral administration of glutamine is approximately between 0.2–0.9 gm/kg/day in at least three divided doses. Preferably, about 0.3 gm/kg/day is administered. It may be administered in any vehicle, as a mixture, in a reconstituted liquid, or the like. Administration may be orally or via a nasogastric tube. Glutamine may also be given in capsule form. Capsules may be acid-resistant slow-release microcapsules.

While the invention has been described with reference to specific embodiments, modifications and variations of the invention may be constructed without departing from the scope of the invention, which is defined in the following claims.

We claim:

1. A method of preventing necrotizing tissue injury in the gastrointestinal tract comprising orally administering glutamine.

2. The method of claim 1, further comprising protecting tissues along the gastrointestinal tract by blocking bacterial translocation with the glutamine.

3. The method of claim 1, further comprising protecting tissues along the gastrointestinal tract with the administered glutamine thereby blocking translocation of bacterial agents, other infectious agents, toxins, chemicals, and injurious substances.

4. The method of claim 1, further comprising optimizing mucosal defense due to an intrluminal/apical presence of the glutamine.

5. The method of claim 1 wherein the administering comprises administering to individuals selected from a group consisting of pre-term infants, full-term infants, children and adults.

6. The method of claim 1 wherein the administering comprises administering glutamine as a powder.

7. The method of claim 1, wherein the administering comprises administering glutamine mixed in a fluid.

8. The method of claim 1, wherein the administering comprises administering glutamine as capsules.

9. The method of claim 8, wherein the capsules are acid-resistant slow-release micro-capsules.

10. The method of claim 8, wherein the capsules are coated acid-resistant slow-release capsules.

11. The method of claim 1, further comprising administering other drugs for treatment of gastrointestinal ailments with the glutamine.

12. The method of claim 2, wherein the blocking bacterial translocation comprises blocking gram (−) bacteria.

13. A method of treating neonatal necrotizing enterocolitis wherein inflammation caused by bacterial translocation and injury is reduced comprising providing enteral glutamine.

14. A method of preventing gastrointestinal dysfunction characterized by infection or inflamation comprising orally administering glutamine and allowing the glutamine to coat gastrointestinal mucosa.

\* \* \* \* \*